(12) United States Patent
Ansari (10) Patent No.: US 7,070,561 B1
(45) Date of Patent: Jul. 4, 2006

(54) ADJUSTABLE WEIGHTED VAGINAL SPECULUM

(76) Inventor: Amir Ansari, 9 Teibrook Ave., Syosset, NY (US) 11791

( * ) Notice: Subject to any disclaimer, the term of this patent is extended or adjusted under 35 U.S.C. 154(b) by 216 days.

(21) Appl. No.: 10/746,986

(22) Filed: Dec. 26, 2003

(51) Int. Cl.
*A61B 1/32* (2006.01)
(52) U.S. Cl. .................................... 600/220
(58) Field of Classification Search ............ 600/184, 600/220, 221, 222, 223
See application file for complete search history.

(56) References Cited

U.S. PATENT DOCUMENTS

| | | | | |
|---|---|---|---|---|
| 831,592 | A * | 9/1906 | Ballard | 600/221 |
| 2,545,201 | A * | 3/1951 | Gilbert | 600/220 |
| 3,565,061 | A * | 2/1971 | Reynolds | 600/220 |
| 3,851,642 | A * | 12/1974 | McDonald | 600/212 |
| 4,202,324 | A * | 5/1980 | Alison | 600/235 |
| 4,337,763 | A * | 7/1982 | Petrassevich | 600/210 |
| 4,638,792 | A * | 1/1987 | Burgin | 600/212 |
| 4,834,067 | A * | 5/1989 | Block | 600/184 |
| 4,884,559 | A * | 12/1989 | Collins | 600/205 |
| 6,394,950 | B1 * | 5/2002 | Weiss | 600/205 |

FOREIGN PATENT DOCUMENTS

WO    WO 9825512    *   6/1998

\* cited by examiner

*Primary Examiner*—Eduardo C. Robert
*Assistant Examiner*—Anuradha Ramana
(74) *Attorney, Agent, or Firm*—Michael I. Kroll (57) ABSTRACT

An adjustable weighted speculum for use during vaginal surgery to separate the vaginal walls. The speculum includes a telescopic blade including a primary blade having first and second ends and a recess extending therethrough, and a secondary blade having a first and second end telescopically positioned within the recess of the primary blade. A handle extends from the second end of the primary blade. A locking mechanism is contained within the handle and connected to the secondary blade for selectively moving the secondary blade or locking the secondary blade in position. A weighted element is releasably attached to the second end of the handle. A plurality of channels extend along a side of the secondary blade from the first end to a point along a length of the secondary blade and a single channel extending along the side of said secondary blade from the second end to the point along the length of the secondary blade wherein the single channel mates with the plurality of channels at the point. A tube may be connected to the single channel for connecting a suction device thereto. A hoop mounted at the second end of the handle allows for selective suspension of the weighted element therefrom, the weighted element may vary in size and weight.

7 Claims, 5 Drawing Sheets

ADJUSTABLE WEIGHTED VAGINAL SPECULUM

BACKGROUND OF THE INVENTION

1. Field of the Invention

The present invention relates generally vaginal surgical instruments and, more specifically, to an adjustable weighted speculum to be used during vaginal surgeries such as dilation and curettage, hysteroscopy, vaginal hysterectomy and other such vaginal procedures in which it is necessary to separate the vaginal walls to provide adequate and constant visualization of the vaginal cavity and access to the uterine cervix and the vaginal apex.

2. Description of the Prior Art

Many speculums have been designed to provide the needed vaginal exposure and to free up the surgeons hands. To accomplish this, weighted speculums are used to place a downward traction on the posterior vaginal wall and to some extent provide separation of the vaginal wall laterally. The lengths of conventional speculum blades are fixed and generally range between 3" and 4". Such conventional speculum blades are frequently dislodged from the vagina. While these units may be suitable for the particular purpose to which they address, they would not be as suitable for the purposes of the present invention as heretofore described.

SUMMARY OF THE PRESENT INVENTION

The present invention relates generally vaginal surgical instruments and, more specifically, to an adjustable weighted speculum to be used during vaginal surgeries such as dilation and curettage, hysteroscopy, vaginal hysterectomy and other such vaginal procedures in which it is necessary to separate the vaginal walls to provide adequate and constant visualization of the vaginal cavity and access to the uterine cervix and the vaginal apex.

A primary object of the present invention is to provide an extendable weighted speculum having a telescopic blade member in which the length of a speculum blade may be adjusted to accommodate the needs of an individual patient.

Another object of the present invention is to provide an extendable weighted speculum having a primary speculum blade substantially similar in shape to conventional speculum blades found on weighted speculums and having a secondary speculum blade residing therein and capable of selectively traveling through and extending beyond the distal end of said primary speculum blade thereby effectively increasing the overall length of the blade assembly.

Another object of the present invention is to provide an extendable weighted speculum having a device for adjusting the blade incorporated within the handle to allow a surgeon to use one hand to adjust the length of the telescopic speculum blades and lock the blade into position with a minimum amount of manual manipulation.

Yet another object of the present invention is to provide an extendable weighted speculum having a removable weighted element allowing for adjusting the weight of the speculum.

A further object of the present invention is to provide an extendable weighted speculum wherein the speculum is disposable and the weighted element or elements are formed from a material suitable for sterilization, preferably stainless steel.

Yet another object of the present invention is to provide an extendable weighted speculum wherein the secondary blade member has a central recess extending longitudinally therethrough with a flexible conduit having a first end attached to an interior end of the central recess and a second end extending to an exterior portion of the speculum and an adaptor for selectively connecting a vacuum source to form an evacuation channel for the removal of smoke or fluids that accumulate inside the vagina and abdomen during surgical procedures.

An even further object of the present invention is to provide an extendable weighted speculum able to avoid spontaneous expulsion from the virginal cavity, which is a commonly encountered problem with the presently available speculums, by adjusting the length of the blades.

Yet another object of the present invention is to provide an extendable weighted speculum that is inexpensive to manufacture and operate.

Still yet another object of the present invention is to provide an extendable weighted speculum that is simple and easy to use.

Additional objects of the present invention will appear as the description proceeds.

The weighted speculum of the present invention is used to place a downward traction on the posterior vaginal wall and, to some extent, provide lateral separation of the vaginal wall. A preferred embodiment includes a substantially vertically extended handle with a primary blade extending angularly outward therefrom at a substantially 90-degree angle. A bottommost portion of the handle includes a weighted element that could be either integral with the handle or attached to the handle. A primary blade extends from the opposite end of the handle. The primary blade has a recess at its extended end, through which a secondary blade is selectively extended. The handle further includes a device for selectively extending the secondary blade member to different lengths and locking the secondary blade into position. The removable weighted element may be used repeatedly in conjunction with disposable speculums wherein the handle and blade members thereof are manufactured of a sturdy plastic composite and stored in sterile hermetically sealed packaging for single use applications.

In addition, when equipped with a sliding spring clip locking mechanism with a semi-rigid cable communicating between the locking mechanism and the secondary blade member and configured in such a manner that the upward movement of the locking mechanism extends the secondary blade member while the downward movement of the locking mechanism retracts the secondary blade member, enabling the surgeon to make the necessary adjustments with only one hand.

In addition, the narrowness of the secondary blade and the combined telescoping capability of the primary and secondary blade members allow the surgeon to easily introduce the tip of the secondary blade member into the abdominal cavity through the opening in the posterior cul de sac during vaginal hysterectomies making the procedure simpler and safer to perform.

Furthermore, an evacuation system may be incorporated at the tip of the adjustable blade with channels extending longitudinally through the secondary blade toward the handle portion of the speculum, where it may be connected to a vacuum source.

The present invention overcomes the shortcomings of the prior art by providing a weighted speculum with a fixed primary blade and a central recess extending longitudinally therethrough to accommodate a secondary blade member that selectively telescopes beyond the distal end of the primary blade member to allow the surgeon to adjust the length of the speculum blade to suit the needs of each individual patient. Further, convenient placement of control devices on the handle of the speculum allow for the surgeon to position the telescopic secondary blade with one hand. Even further, the speculum of the present invention incorporates evacuation channels through the blades for attaching to a suction device, further increasing the operative convenience of the present invention.

To the accomplishment of the above related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to those skilled in the art to practice the invention, and it is to be understood that other embodiments may be utilized and that structural changes may be made without departing from the scope of the invention. In the accompanying drawings, like reference characters designate the same or similar parts throughout the several views.

DESCRIPTION OF THE REFERENCED NUMERALS

Turning now descriptively to the drawings, in which similar reference characters denote similar elements throughout the several views, the Figures illustrate the adjustable weighted speculum of the present invention. With regard to the reference numerals used, the following numbering is used throughout the various drawing figures.

10 adjustable weighted vaginal speculum of the present invention
12 extendable telescopic blade
14 primary blade member
16 secondary blade member
18 handle
20 central recess
22 first end of the primary blade member
24 second end of the primary blade member
26 first end of the secondary blade member
28 second end of the secondary blade member
30 a plurality of channels
32 single channel
36 loop
38 hook
40 weighted element
42 tube
44 adaptor
46 cable
48 handle recess
49 slot
50 spring clip
52 knob
53 lever
54 notch
60 first end of slot
61 second end of slot

DETAILED DESCRIPTION OF THE DRAWING FIGURES

Turning now descriptively to the drawings, in which similar reference characters denote similar elements throughout the several views, FIGS. 1 through 5 illustrate the adjustable weighted vaginal speculum of the present invention indicated generally by the numeral 10.

Figure 1:
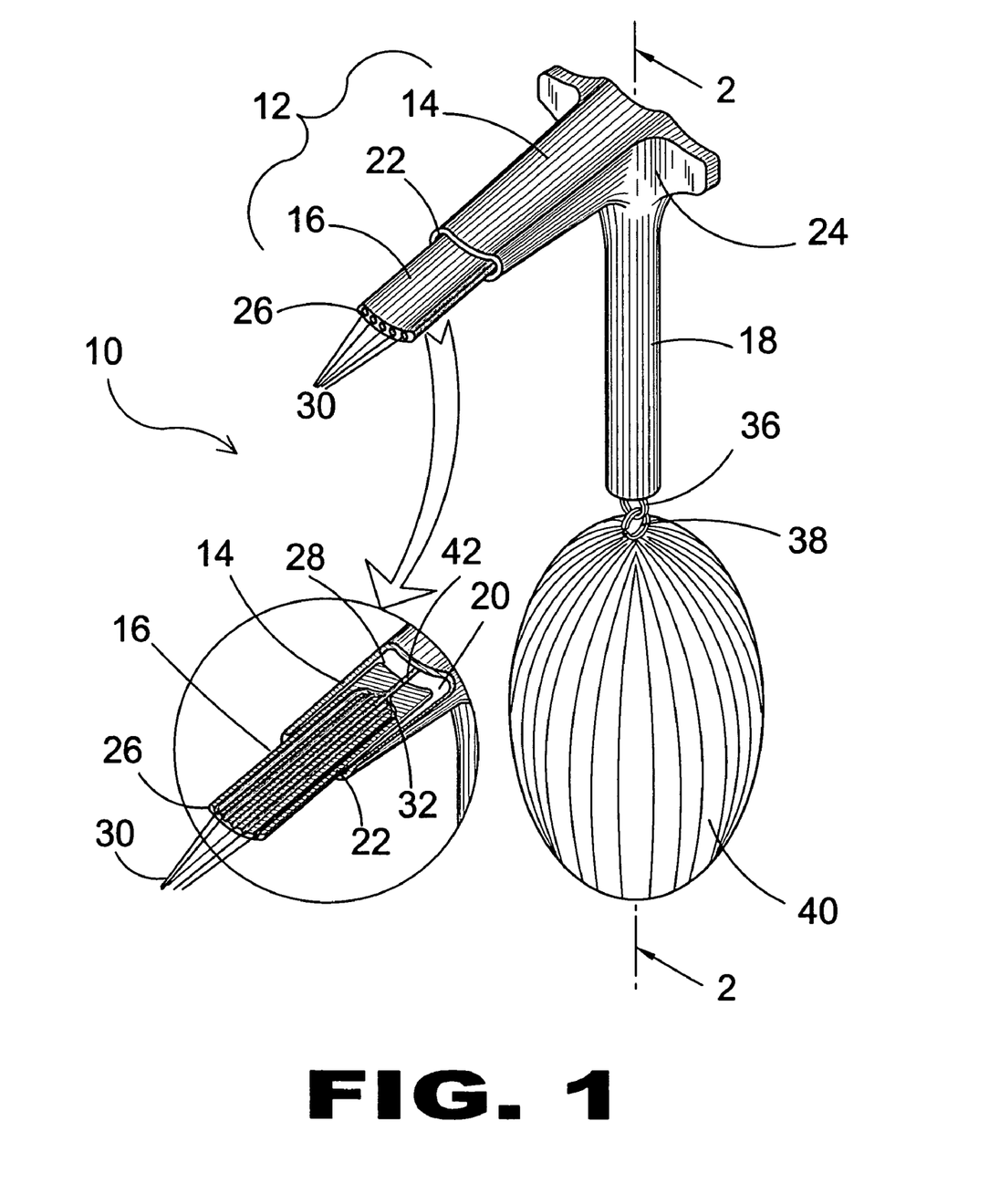
FIG. 1 is a perspective view of the adjustable weighted vaginal speculum of the present invention and a cross sectional view of the secondary blade thereof.

FIG. 1 is a perspective view of the adjustable weighted vaginal speculum 10 of the present invention having an extendable telescopic blade 12. The telescopic blade 12 includes a primary blade member 14 and a secondary blade member 16. The secondary blade member 16 travels within the primary blade member 14. A cross sectional view of the secondary blade member 16 is also shown in this Figure. A handle 18 extends at preferably a substantially 90-degree angle from the telescopic blade 12 to form the adjustable weighted speculum 10 of the present invention. The primary blade member 14 is fixed in position and shaped in a flattened oval form. The primary blade member 14 includes a first end 22 and a second end 24. A central recess 20 extends through the primary blade member 14 between the first and second ends 22 and 24, respectfully. The central recess 20 accommodates the secondary blade member 16 therein whereby the secondary blade member is able to selectively telescope beyond the first end 22 of the primary blade member 14.

The secondary blade member 16 has a first end 26 and a second end 28 and has a flattened oval shape. When fully retracted, the first end 26 of the secondary blade member 16 aligns with the first end 22 of the primary blade member 14. In this position the secondary blade member 16 is fully contained within the central recess 20 of the primary blade member 14. A plurality of channels 30 extend longitudinally from the first end 26 of the secondary blade member 16 and meet at a point along a length of the secondary blade member 16. A single channel 32 extends longitudinally from the second end 28 to a point along the length of the secondary blade member 16. The plurality of channels 30 meet within the secondary blade member 16 at the single channel 32. A tube 42 is attached to the single channel 32 at the second end of the secondary blade member 16 for providing suction to the plurality of channels 30 extending from the first end 26 of the secondary blade member 16.

The handle 18 is ergonomically shaped so as to be comfortably grasped by a hand of a surgeon. The handle 18 extends from the second end 24 of the primary blade member 14. The handle 18 preferably extends at an angle of substantially 90 degrees to the primary blade member 14. However, the handle 18 may extend at any useful angle from the primary blade member or at any point along the length of the primary blade member 14. A loop 36 is mounted to the handle 18 at an end opposite the connection to the primary blade member 14. A weighted element 40 includes a hook 38 attached thereto. The weighted element 40 is selectively suspended from the loop 36 via the hook 38. The weighted element 40 may be removed from its selective connection to the speculum 10 and thus used repeatedly. The handle 18 and extendable telescopic blade 12 of the speculum 10 are preferably manufactured of a sturdy plastic composite and stored in sterile hermetically sealed packaging for single use applications. Alternatively, the weighted element 40 may be integrally formed with the handle 18 and thus would not be reusable with other speculums. However, using a weighted element 40 which is removably connected to the handle 18 allows for the weight applied to the speculum 10 to be adjusted depending upon the patient's needs.

Figure 2:
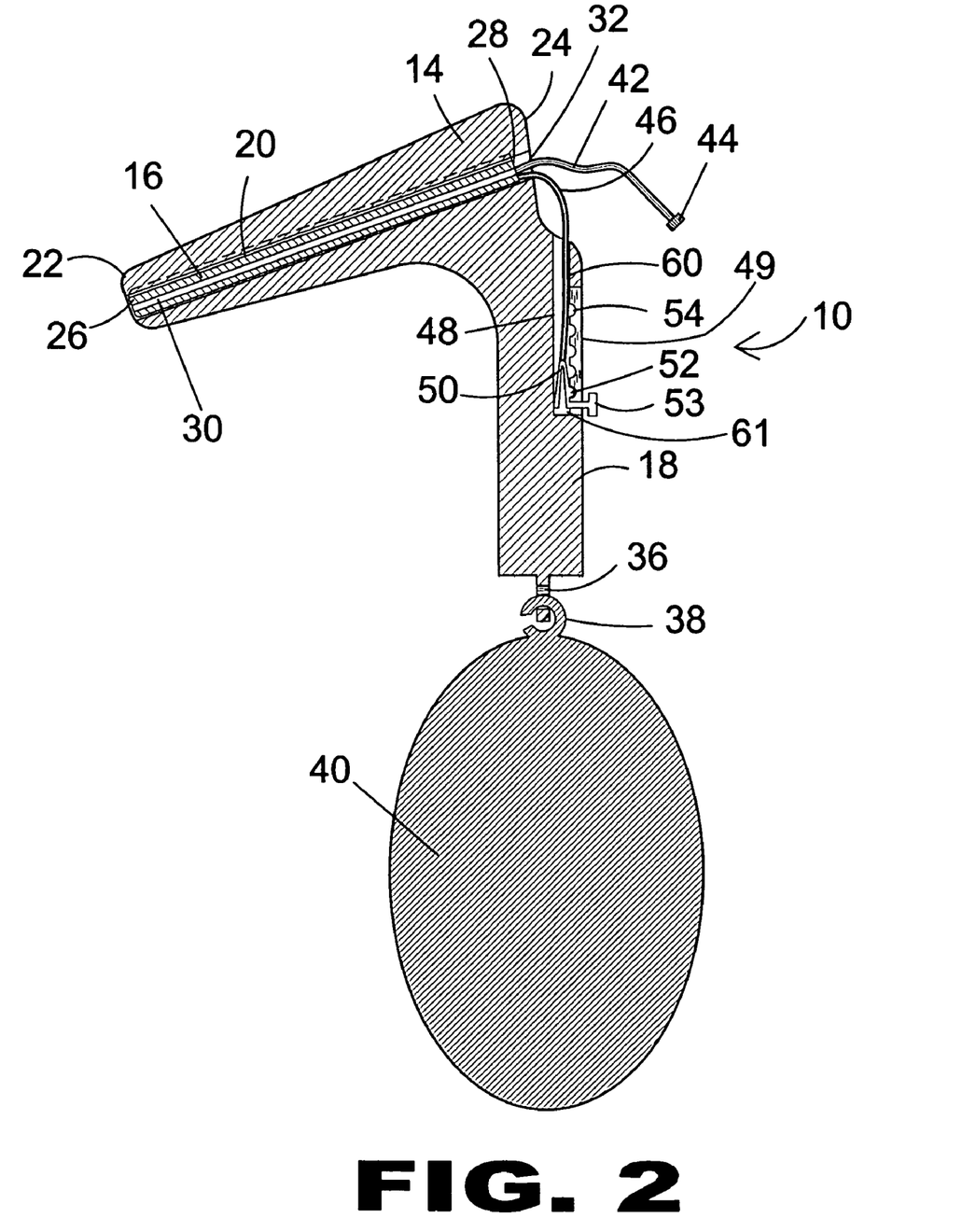
FIG. 2 is a cross sectional view of the adjustable weighted vaginal speculum of the present invention showing the secondary blade member in a fully retracted position taken along line 2—2 if FIG. 1.

FIG. 2 is a cross sectional view of the adjustable weighted vaginal speculum 10 of the present invention taken along the line 2—2 of FIG. 1. This figure shows the secondary blade member 16 locked in a fully retracted position by a spring clip locking mechanism 50. The telescopic blade 12 and handle 18 preferably extend at a substantially 90-degree angle from one another to form the adjustable weighted speculum 10. The telescopic blade 12 includes the fixed primary blade 14 having a flattened oval form with a central recess 20 extending longitudinally therethrough between the first and second ends, 22 and 24 respectively. This recess 20 accommodates the secondary blade member 16. The secondary blade member 16 may be fully received within the central recess 20 and is selectively telescopic to extend a distance out of the central recess 20 and beyond the first end 22 of the primary blade member 14.

The secondary blade member 16 also has a flattened oval shape. When in a fully retracted position, the first end 26 of the secondary blade member 16 is fully received within the central recess and is in alignment with the first end 22 of the primary blade member 14. A plurality of channels 30 extend longitudinally from the first end 26 of the secondary blade member 16 and meet at a point along the length of the secondary blade member 16. A single channel 32 extends from the second end 28 to a point along the length of the secondary blade member 16. The plurality of channels 30 meet at the single channel 32. A tube 42 is attached to the single channel 32 at the second end 28 of the secondary blade member 16. The tube 42 extends from the channel 32, and is of a length whereby, if the secondary blade member 16 is fully extended from the primary member 14, the tube 42 extends into the central recess 20 beyond the second side 24 of the primary blade member 14. The end of the tube 42 opposite the channel 32 is able to be attached to an adaptor 44 for connecting to a vacuum.

The handle 18 is ergonomically shaped so as to be comfortably grasped by a hand of a surgeon. The handle 18 extends from the second end 24 of the primary blade member 14. The handle 18 preferably extends at an angle of substantially 90 degrees to the primary blade member 14. However, the handle 18 may extend at any useful angle from the primary blade member or at any point along the length of the primary blade member 14. A loop 36 is mounted to the handle 18 at an end opposite the connection to the primary blade member 14. A weighted element 40 includes a hook 38 attached thereto. The weighted element 40 is selectively suspended from the loop 36 via the hook 38. The weighted element 40 may be removed from its selective connection to the speculum 10 and thus used repeatedly. The handle 18 and extendable telescopic blade 12 of the speculum 10 are preferably manufactured of a sturdy plastic composite and stored in sterile hermetically sealed packaging for single use applications. Alternatively, the weighted element 40 may be integrally formed with the handle 18 and thus would not be reusable with other speculums. However, using a weighted element 40 which is removably connected to the handle 18 allows for the weight applied to the speculum 10 to be adjusted depending upon the patient's needs.

A recess 48 extends longitudinally at least partially into the handle 18. A slot 49 extends into the recess 48 from the exterior of the handle 18. The slot 49 extends along at lease a portion of the recess 48. The length of the slot 49 is defined by a first top end 60 and a second bottom end 61. A plurality of grooves 54 are aligned along the recess adjacent to the slot 49. A spring clip 50 extends through the slot 49 and into the recess 48, a tab 53 is connected to the spring clip 50 and is positioned on the side of the slot 49 opposite the recess 48. A knob 52 extends from the spring clip 50, and is received by a selected one of the plurality of grooves 54. The spring clip 50 is selectively able to slide along the slotted portion of the recess 48. When the knob 52 is fitted within one of the plurality of grooves 54, the spring clip 50 is prevented from sliding along the slot. A cable 46 is connected at a first end to the secondary blade member 16 and extends into the recess 48. A second end of the cable 46 is connected to the spring clip 50. Moving the spring clip 50 a distance longitudinally along the slot 49 causes the secondary blade member 16 to move an equal distance along the central recess 20 of the primary blade member 14. Pressing the tab 53 causes the knob 52 to be removed from engagement with the selected one of the plurality of groves 54 allowing for the movement of the spring clip longitudinally along the slotted portion of the recess 48. The slotted portion of the recess 48 defines the distance that a user of the adjustable weighted speculum 10 is able to telescopically extend the secondary blade member 16 beyond the first end 22 of the primary blade member 14.

As illustrated, the knob 52 is gripping one of the plurality of grooves 54 positioned nearest the second end 61 of the slot 49. By gripping the grooved wall at such a position, the secondary blade member 16 is locked in a fully retracted position with the first end 26 of the secondary blade member 16 aligned with the first end 22 of the primary blade member 14.

Figure 3:
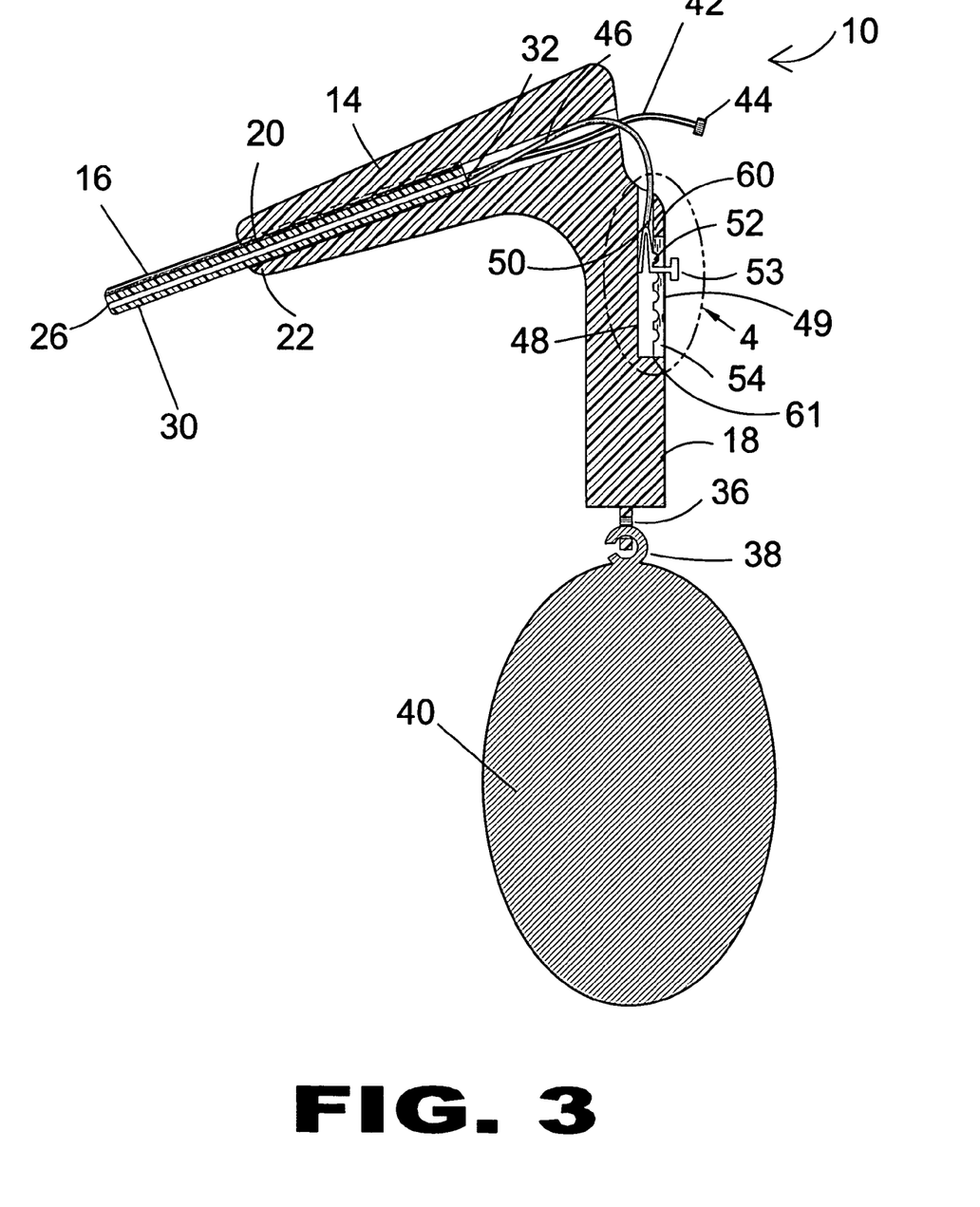
FIG. 3 is a cross sectional view of the adjustable weighted vaginal speculum of the present invention showing the secondary blade member locked in a fully extended position taken along line 2—2 of FIG. 1.

FIG. 3 is a cross sectional view taken along line 2—2 of FIG. 1 of the adjustable weighted vaginal speculum 10 of the present invention showing the secondary blade member 16 locked in a fully extended position by the spring clip 50 locking mechanism. This figure shows the secondary blade member 16 locked in a fully extended position by the spring clip 50 locking mechanism. The telescopic blade 12 and handle 18 extend at a substantially 90-degree angle from one another to form the adjustable weighted speculum 10. The telescopic blade 12 includes the fixed primary blade 14 having a flattened oval form with a central recess 20 extending longitudinally therethrough between the first and second ends, 22 and 24 respectively. This recess 20 accommodates the secondary blade member 16. The secondary blade member 16 may be fully received within the central recess 20 and is selectively telescopic to extend a distance out of the central recess 20 and beyond the first end 22 of the primary blade member 14.

The secondary blade member 16 also has a flattened oval shape. When in a fully retracted position, the first end 26 of the secondary blade member 16 is fully received within the central recess and is in alignment with the first end 22 of the primary blade member 14. A plurality of channels 30 extend longitudinally from the first end 26 of the secondary blade member 16 and meet at a point along the length of the secondary blade member 16. A single channel 32 extends from the second end 28 to a point along the length of the secondary blade member 16. The plurality of channels 30 meet at the single channel 32. A tube 42 is attached to the single channel 32 at the second end 28 of the secondary blade member 16. The tube 42 extends from the channel 32, and is of a length whereby, if the secondary blade member 16 is fully extended from the primary member 14, the tube 42 extends into the recess beyond the second side 24 of the primary blade member 14. The end of the tube 42 opposite the channel 32 is able to be attached to an adaptor 44 for connecting to a vacuum.

The handle 18 is ergonomically shaped so as to be comfortably grasped by a hand of a surgeon. The handle 18 extends from the second end 24 of the primary blade member 14. The handle 18 preferably extends at an angle of substantially 90 degrees to the primary blade member 14. However, the handle 18 may extend at any useful angle from the primary blade member or at any point along the length of the primary blade member 14. A loop 36 is mounted to the handle 18 at an end opposite the connection to the primary blade member 14. A weighted element 40 includes a hook 38 attached thereto. The weighted element 40 is selectively suspended from the loop 36 via the hook 38. The weighted element 40 may be removed from its selective connection to the speculum 10 and thus used repeatedly. The handle 18 and extendable telescopic blade 12 of the speculum 10 are preferably manufactured of a sturdy plastic composite and stored in sterile hermetically sealed packaging for single use applications. Alternatively, the weighted element 40 may be integrally formed with the handle 18 and thus would not be reusable with other speculums. However, using a weighted element 40 which is removably connected to the handle 18 allows for the weight applied to the speculum to be adjusted depending upon the patient's needs.

A recess 48 extends longitudinally at least partially into the handle 18. A slot 49 extends into the recess 48 from the exterior of the handle 18. The slot 49 extends along at lease a portion of the recess 48. The length of the slot 49 is defined by a first top end 60 and a second bottom end 61. A plurality of grooves 54 are aligned along the recess adjacent to the slot 49. A spring clip 50 extends through the slot 49 and into the recess 48, a tab 53 is connected to the spring clip 50 and is positioned on the side of the slot 49 opposite the recess 48. A knob 52 extends from the spring clip 50, and is received by a selected one of the plurality of grooves 54. The spring clip 50 is selectively able to slide along the slotted portion of the recess 48. When the knob 52 is fitted within one of the plurality of grooves 54, the spring clip 50 is prevented from sliding along the slot. A cable 46 is connected at a first end to the secondary blade member 16 and extends into the recess 48. A second end of the cable 46 is connected to the spring clip 50. Moving the spring clip 50 a distance longitudinally along the slot 49 causes the secondary blade member 16 to move an equal distance along the central recess 20 of the primary blade member 14. Pressing the tab 53 causes the knob 52 to be removed from engagement with the selected one of the plurality of groves 54 allowing for the movement of the spring clip longitudinally along the slotted portion of the recess 48. The slotted portion of the recess 48 defines the distance that a user of the adjustable weighted speculum 10 is able to telescopically extend the secondary blade member 16 beyond the first end 22 of the primary blade member 14.

As illustrated, the knob 52 is gripping one of the plurality of grooves 54 positioned nearest the first end 60 of the slot 49. By gripping the grooved wall 54 at such a position, the secondary blade member 16 is locked in a fully extended position with the first end 26 of the secondary blade member 16 protruding from the first end 22 of the primary blade member 14.

Figure 4:
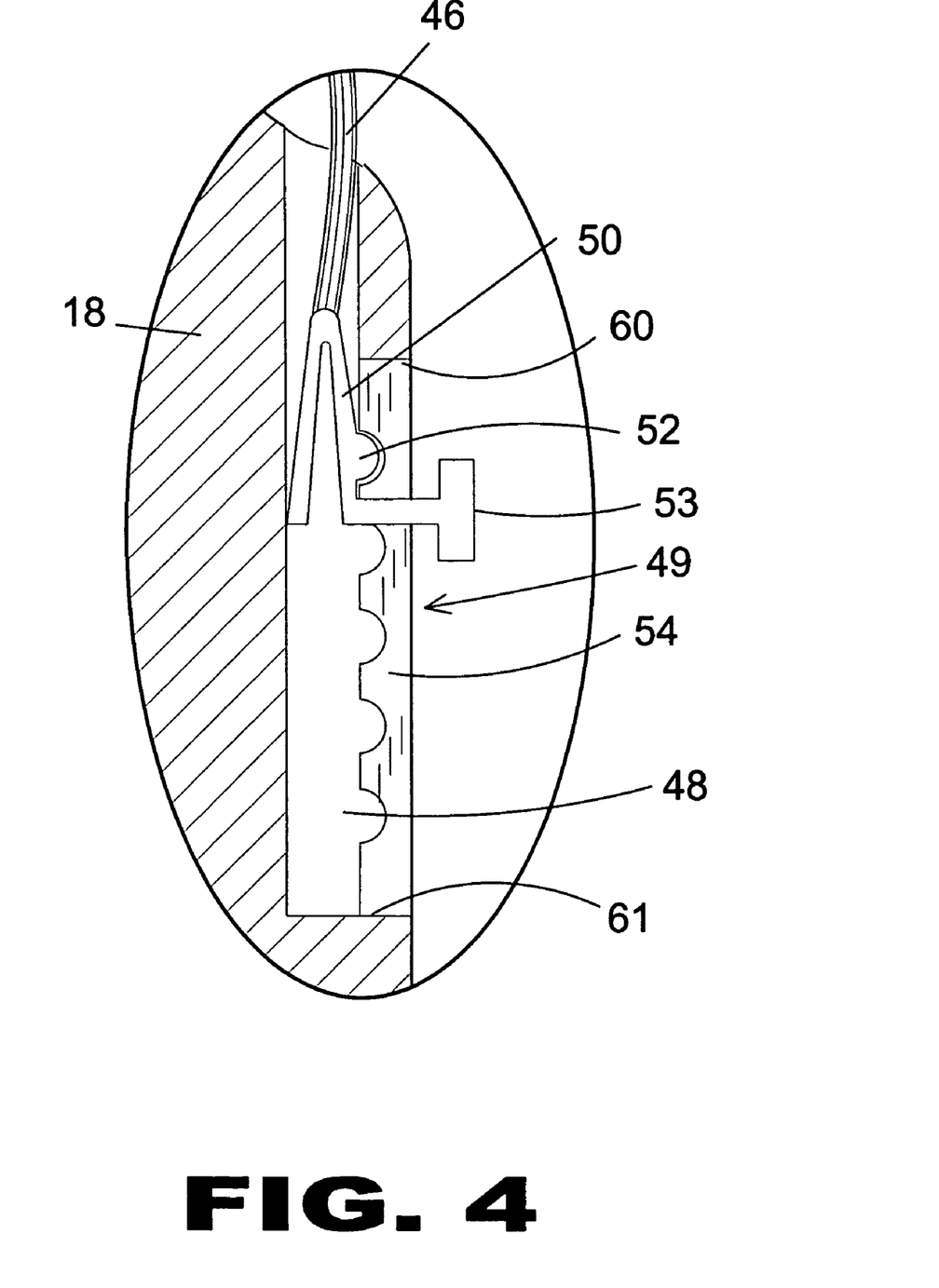
FIG. 4 is an enlarged view of the locking mechanism of the adjustable weighted vaginal speculum of the present invention taken within the circular area identified by numeral 4 in FIG. 3.

FIG. 4 is a detailed enlargement of the circular area labeled as 4 in FIG. 3 showing one embodiment of the locking mechanism of the present invention. The locking mechanism is formed by a recess 48, which extends longitudinally at least partially into the handle 18. A slot 49 extends into the recess 48 from the exterior of the handle 18. The slot 49 extends along at lease a portion of the recess 48. The length of the slot 49 is defined by a first top end 60 and a second bottom end 61. A plurality of grooves 54 are aligned along the recess adjacent to the slot 49. A spring clip 50 extends through the slot 49 and into the recess 48, a tab 53 is connected to the spring clip 50 and is positioned on the side of the slot 49 opposite the recess 48. A knob 52 extends from the spring clip 50, and is received by a selected one of the plurality of grooves 54. The spring clip 50 is selectively able to slide along the slotted portion of the recess 48. When the knob 52 is fitted within one of the plurality of grooves 54, the spring clip 50 is prevented from sliding along the slot. A cable 46 is connected at a first end to the secondary blade member 16 and extends into the recess 48. A second end of the cable 46 is connected to the spring clip 50. Moving the spring clip 50 a distance longitudinally along the slot 49 causes the secondary blade member 16 to move an equal distance along the central recess 20 of the primary blade member 14. Pressing the tab 53 causes the knob 52 to be removed from engagement with the selected one of the plurality of groves 54 allowing for the movement of the spring clip longitudinally along the slotted portion of the recess 48. The slotted portion of the recess 48 defines the distance that a user of the adjustable weighted speculum 10 is able to telescopically extend the secondary blade member 16 beyond the first end 22 of the primary blade member 14.

As illustrated, the knob 52 is gripping one of the plurality of grooves 54 positioned nearest the first end 60 of the slot 49. By gripping the grooved wall 54 at such a position, the secondary blade member 16 is locked in a fully extended position with the first end 26 of the secondary blade member 16 protruding from the first end 22 of the primary blade member 14. The extent of extension of the secondary blade member 16 is dependant upon the position of the spring clip 50 within the slot 49 and the groove within which the knob 52 is engaged.

Figure 5:
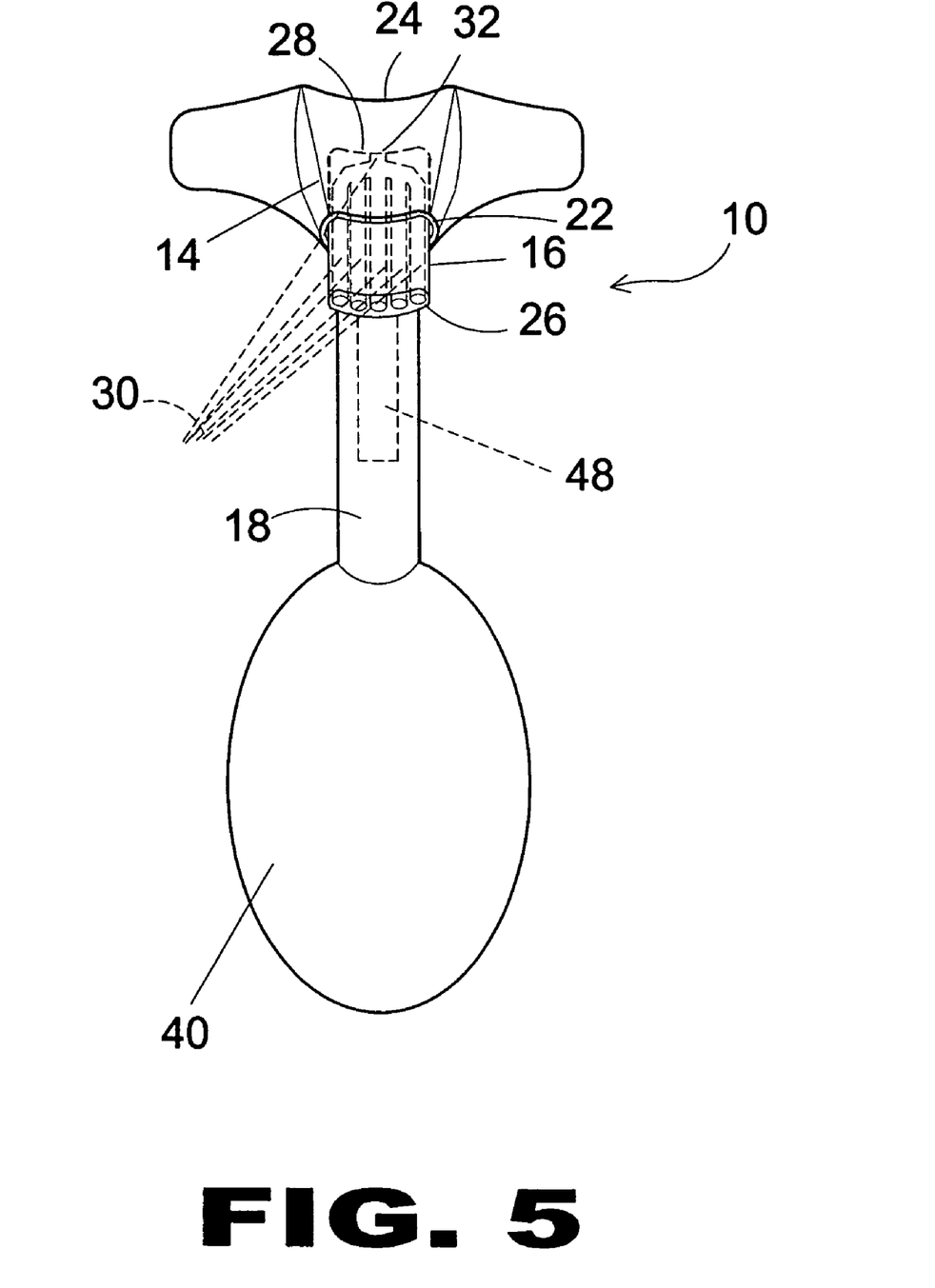
FIG. 5 is a front view of the adjustable weighted vaginal speculum of the present invention having a weighted element integrated with the handle thereof.

FIG. 5 is a front view of the adjustable weighted vaginal speculum 10 of the present invention having a weighted element 40 integrated with the handle thereof. The telescopic blade 12 includes a primary blade member 14 and a secondary blade member 16. The secondary blade member 16 travels within the primary blade member 14. A cross sectional view of the secondary blade member 16 is also shown in this Figure. A handle 18 extends at preferably a substantially 90-degree angle from the telescopic blade 12 to form the adjustable weighted speculum 10 of the present invention. The primary blade member 14 is fixed in position and shaped in a flattened oval form. The primary blade member 14 includes a first end 22 and a second end 24. A central recess 20 extends through the primary blade member 14 between the first and second ends 22 and 24, respectfully. The central recess 20 accommodates the secondary blade member 16 therein whereby the secondary blade member is able to selectively telescope beyond the first end 22 of the primary blade member 14.

The secondary blade member 16 has a first end 26 and a second end 28 and has a flattened oval shape. When fully retracted, the first end 26 of the secondary blade member 16 aligns with the first end 22 of the primary blade member 14. In this position and the secondary blade member 16 is fully contained within the central recess 20 of the primary blade member 14. A plurality of channels 30 extend longitudinally from the first end 26 of the secondary blade member 16 and meet at a point along a length of the secondary blade member 16. A single channel 32 extends longitudinally from the second end 28 to a point along the length of the secondary blade member 16. The plurality of channels 30 meet within the secondary blade member 16 at the single channel 32. A tube 42 is attached to the single channel 32 at the second end of the secondary blade member 16 for providing suction to the plurality of channels 30 extending from the first end 26 of the secondary blade member 16.

The handle 18 is ergonomically shaped so as to be comfortably grasped by a hand of a surgeon. The handle 18 extends from the second end 24 of the primary blade member 14. The handle 18 preferably extends at an angle of substantially 90 degrees to the primary blade member 14. However, the handle 18 may extend at any useful angle from the primary blade member or at any point along the length of the primary blade member 14. The weighted element 40 is integrally formed with the handle 18 at an end opposite that of the primary blade member 14. Such an embodiment of the speculum is preferably manufactured of a sturdy plastic composite and stored in sterile hermetically sealed packaging for single use applications.

In operation, the telescopic blade of the present invention is inserted into the vaginal cavity of a prospective patient while in the fully retracted position. Prior to use the secondary blade member 16 is in the fully retracted position completely received within the recess of the primary blade member. In this position the spring clip is positioned at the bottom second end of the slot with the knob engaged with the groove closest to the bottom second end of the slot. Once inserted, the surgeon may extend the secondary blade member further into the vaginal cavity to avoid spontaneous expulsion of the speculum, a commonly encountered problem with presently available and conventional speculums. In order to extend the secondary blade member, the surgeon grasps the handle of the speculum and applies pressure on the tab towards the handle. The pressure releases the knob from its engagement in a groove. A force is then exerted on the tab in a direction towards the top of the slot. As the tab is moved towards the top of the slot the knob and spring clip move with the tab forcing a length of the cable to extend from the recess. As the cable exits the recess a pressure is applied to the secondary blade member causing the secondary blade member to extend out of the recess in the primary blade member. Once the blade is extended to a desired depth, a weighted element is suspended from the loop to place a downward pressure on the posterior vaginal wall and to some extent provide separation of the vaginal wall laterally. Such separation allows the surgeon/doctor adequate and constant visualization of the vaginal cavity and access to the uterine cervix and the vaginal apex. A suction device may be connected to the adaptor of a tube extending from the telescopic blade. The suction is provided through the tube to the plurality of recesses within the secondary blade member for removing excess fluids or smoke that may accumulate during an examination or surgical procedure. When the procedure is complete, the surgeon reapplies pressure to the tab to disengage the knob from the groove. A pressure is then applied to the tab in a direction towards the bottom of the slot causing the secondary blade member to be retracted back into the primary blade member. Once retracted, the pressure on the tab is removed and the speculum is removed from the vaginal area.

The surgeon is able to easily position the adjustable weighted speculum and extend or retract the telescopic blade member thereof with the use of one hand. This is made possible by the convenient placement of the locking device within the handle. By pressing and sliding the handle, the user may position the secondary blade member to a desired depth within the vaginal cavity. When the tab is released, the secondary blade member is locked into position. The narrowness of the secondary blade and the combined telescopic capability of the two blade members also permits the surgeon to easily introduce the tip of the of the secondary blade member into the abdominal cavity through the opening in the posterior cul de sac during virginal hysterectomies making the procedure simpler and safer to perform.

From the above description it can be seen that the present invention overcomes the shortcomings of the prior art by providing an adjustable weighted speculum with a fixed primary blade member and a central recess extending longitudinally therethrough to accommodate a secondary blade member that selectively telescopes beyond the distal end of the primary blade member to allow the surgeon to adjust the length of the speculum blade accordingly to suit the needs of each individual patient. Further, the adjustable weighted vaginal speculum allows for convenient placement of control devices on the handle thereby allowing the surgeon to position the telescopic secondary blade with the use of one hand. Additionally, the adjustable weighted vaginal speculum of the present invention incorporates evacuation channels extending longitudinally through the blades that when attached to a suction device for removing smoke or fluids which may accumulate during a surgical procedure, thus increasing the operative convenience of the present invention and increasing the visibility of an operative surgeon while delimiting the number of surgical instruments necessary to perform the necessary surgical procedures. Furthermore, the adjustable weighted vaginal speculum of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. An adjustable weighted speculum, comprising:
   a) a telescopic blade including a primary blade having a first end; a second end and a recess extending therethrough between said first and second ends; and a secondary blade having a first end and a second end, said secondary blade being received within said recess of said primary blade and movable between a first position substantially completely received within said recess of said primary blade and a second position extending at least partially from said recess of said primary blade;
   b) a handle extending from said second end of said primary blade;
   c) a locking mechanism attached to said handle and connected to said second end of said secondary blade for controlling movement of said secondary blade between said first and second positions;
   d) a weighted element releasably attached to said handle, and
   e) a plurality of channels extending along a side of said secondary blade from said first end to a point along a length of said secondary blade and a single channel extending along said side of said secondary blade from said second end to said point along said length of said secondary blade wherein said single channel mates with said plurality of channels at said point.

2. The speculum as recited in claim 1, further comprising a tube extending from said single channel and having a length greater than a length of said primary blade, an adaptor attached to an end of said tube opposite said single channel and a suction device connected to said adapter for providing suction to said single channel.

3. The speculum as recited in claim 1, further comprising a hoop mounted at an end of said handle opposite said telescopic blade for selectively suspending said weighted element therefrom.

4. The speculum as recited in claim 3, wherein said weighted element is adjustable to releasably secure any desired weight amount to said handle.

5. The speculum as recited in claim 1, wherein said locking mechanism includes a recess extending into said handle; a slot extending along at least a portion of said recess providing access to said recess from an outer side of said handle, a spring clip extending through said slot and into said recess, said spring clip including a knob protruding from an end of said spring clip within said handle and a tab extending from a side of said spring clip opposite said knob and located on a side of said slot opposite said recess wherein said recess includes a plurality of notches extending along a side thereof adjacent and parallel said slot for selectively receiving said knob within a selective one of said notches; and a cable connected between said second end of said secondary blade and said spring clip wherein said cable causes said secondary blade to move in a telescoping manner within said recess in said primary blade upon movement of said spring clip along a length of said slot.

6. The speculum as recited in claim 5, wherein application of a force to said tab in a direction towards said recess causes said knob to become disengaged from a respective notch and thereby allow movement of said clip along said length of said slot thereby moving said secondary blade between said first and second positions.

7. The speculum as recited in claim 6, wherein removal of said force on said tab causes said knob to engage with a respective one of said plurality of notches closest the position of the knob upon removal of said force.

* * * * *